(12) United States Patent
Menavsky et al.

(10) Patent No.: US 12,040,078 B2
(45) Date of Patent: Jul. 16, 2024

(54) DENTAL IMAGE ANALYSIS AND TREATMENT PLANNING USING AN ARTIFICIAL INTELLIGENCE ENGINE

(71) Applicants: Edward Menavsky, Malibu, CA (US); Pavel Polupan, Malibu, CA (US)

(72) Inventors: Edward Menavsky, Malibu, CA (US); Pavel Polupan, Malibu, CA (US)

(*) Notice: Subject to any disclaimer, the term of this patent is extended or adjusted under 35 U.S.C. 154(b) by 858 days.

(21) Appl. No.: 17/075,230

(22) Filed: Oct. 20, 2020

(65) Prior Publication Data

US 2021/0134440 A1 May 6, 2021

Related U.S. Application Data

(60) Provisional application No. 62/931,498, filed on Nov. 6, 2019.

(51) Int. Cl.
| | |
|---|---|
| *G06T 7/00* | (2017.01) |
| *G06T 11/00* | (2006.01) |
| *G16H 10/20* | (2018.01) |
| *G16H 15/00* | (2018.01) |
| *G16H 30/20* | (2018.01) |
| *G16H 30/40* | (2018.01) |
| *G16H 40/20* | (2018.01) |
| *G16H 50/20* | (2018.01) |
| *G16H 50/30* | (2018.01) |
| *G16H 50/70* | (2018.01) |

(52) U.S. Cl.
CPC ............ *G16H 30/40* (2018.01); *G06T 7/0014* (2013.01); *G06T 11/00* (2013.01); *G16H 10/20* (2018.01); *G16H 15/00* (2018.01); *G16H 30/20* (2018.01); *G16H 40/20* (2018.01); *G16H 50/20* (2018.01); *G16H 50/30* (2018.01); *G16H 50/70* (2018.01); *G06T 2207/20076* (2013.01); *G06T 2207/20081* (2013.01); *G06T 2207/20084* (2013.01)

(58) Field of Classification Search
CPC ........ G16H 40/20; G16H 15/00; G16H 10/20; G06T 7/0014; G06T 11/00
See application file for complete search history.

(56) References Cited

U.S. PATENT DOCUMENTS

| | | | | |
|---|---|---|---|---|
| 10,984,529 | B2* | 4/2021 | Carter | G16H 50/20 |
| 2016/0135925 | A1* | 5/2016 | Mason | A61C 7/002 |
| | | | | 703/2 |
| 2021/0074425 | A1* | 3/2021 | Carter | G06V 10/25 |
| 2023/0386045 | A1* | 11/2023 | Amelon | A61B 5/4547 |

* cited by examiner

*Primary Examiner* — Edward Park
(74) *Attorney, Agent, or Firm* — Intrinsic Law Corp.

(57) ABSTRACT

A trained artificial intelligence engine analyzes a subject's dental images and dental survey results to determine whether the subject has an apparent dental condition. The artificial intelligence engine is trained using manually-classified dental images and model survey results. The trained artificial intelligence engine can annotate the subject's dental images to indicate landmark structures and the location of the apparent dental condition. In addition, the trained artificial intelligence engine can generate a confidence score that indicates the likelihood that the subject has the apparent dental condition.

9 Claims, 15 Drawing Sheets

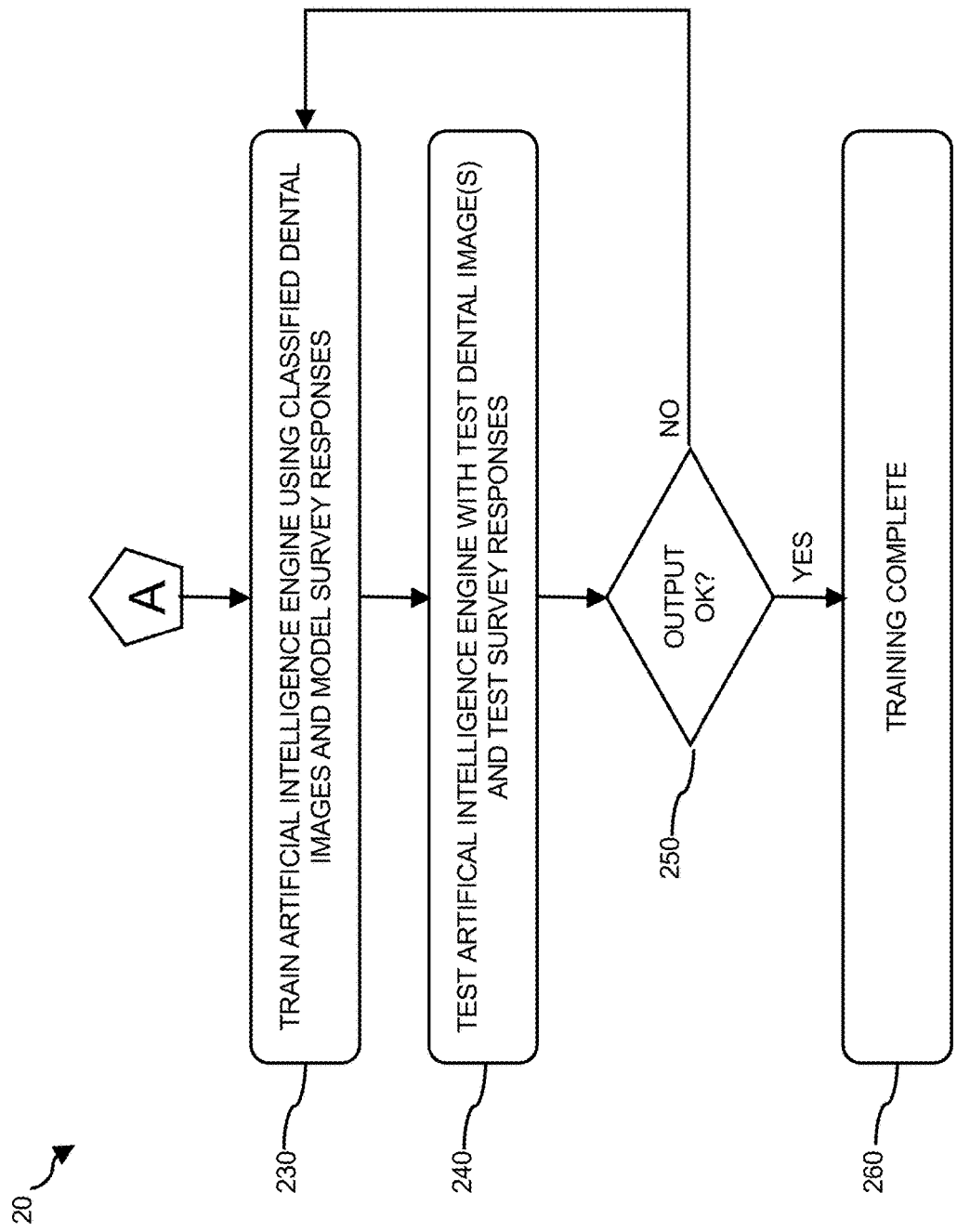

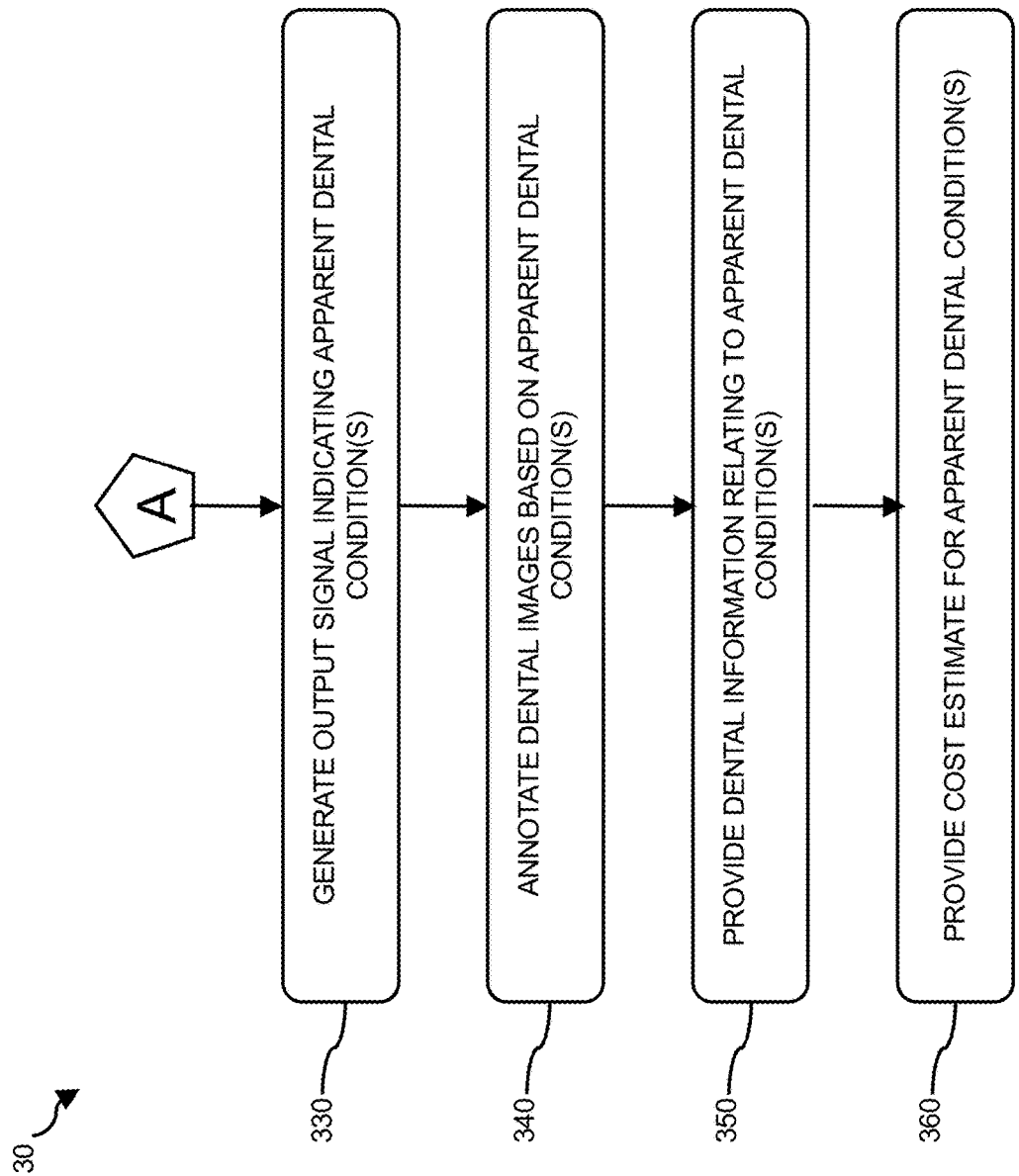

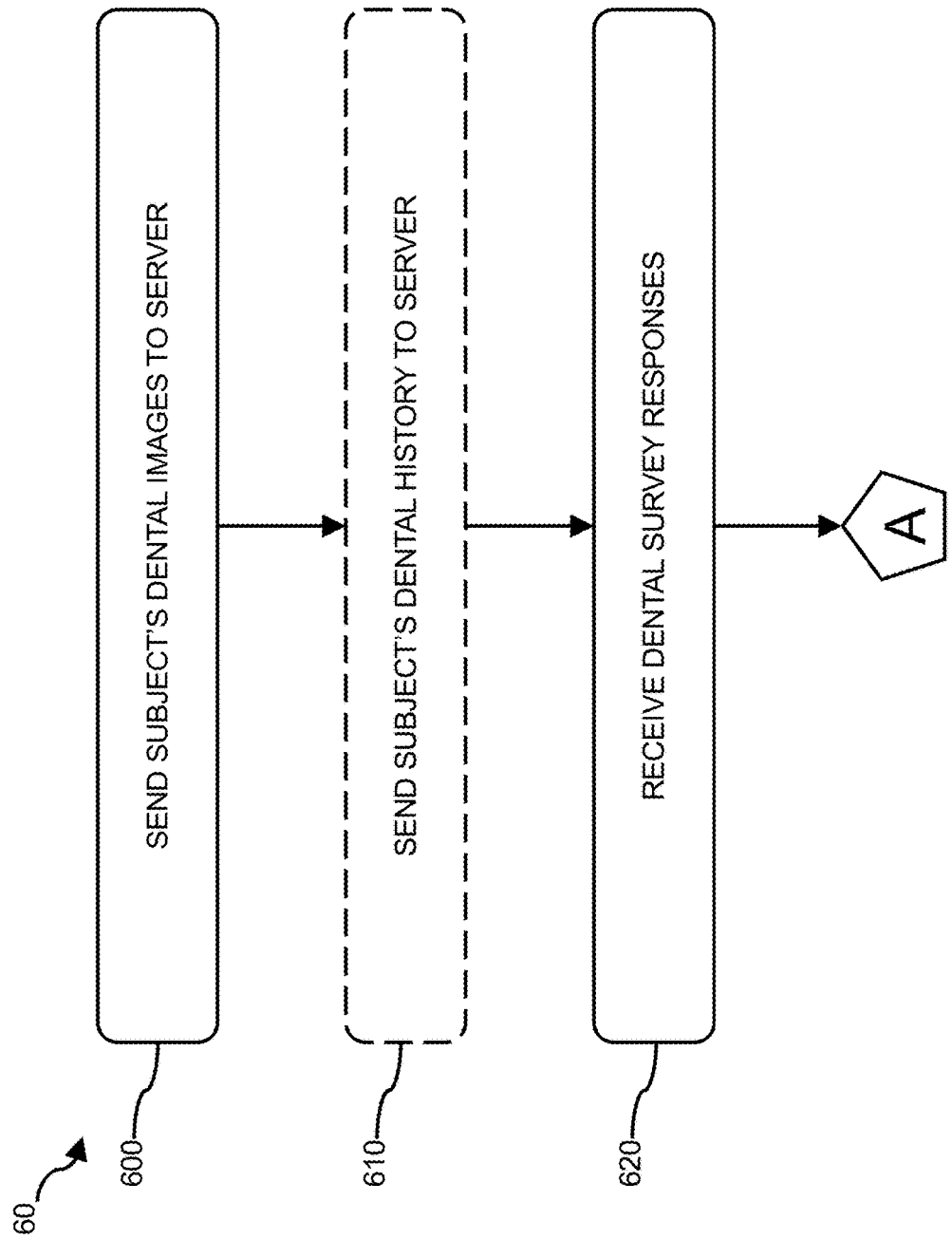

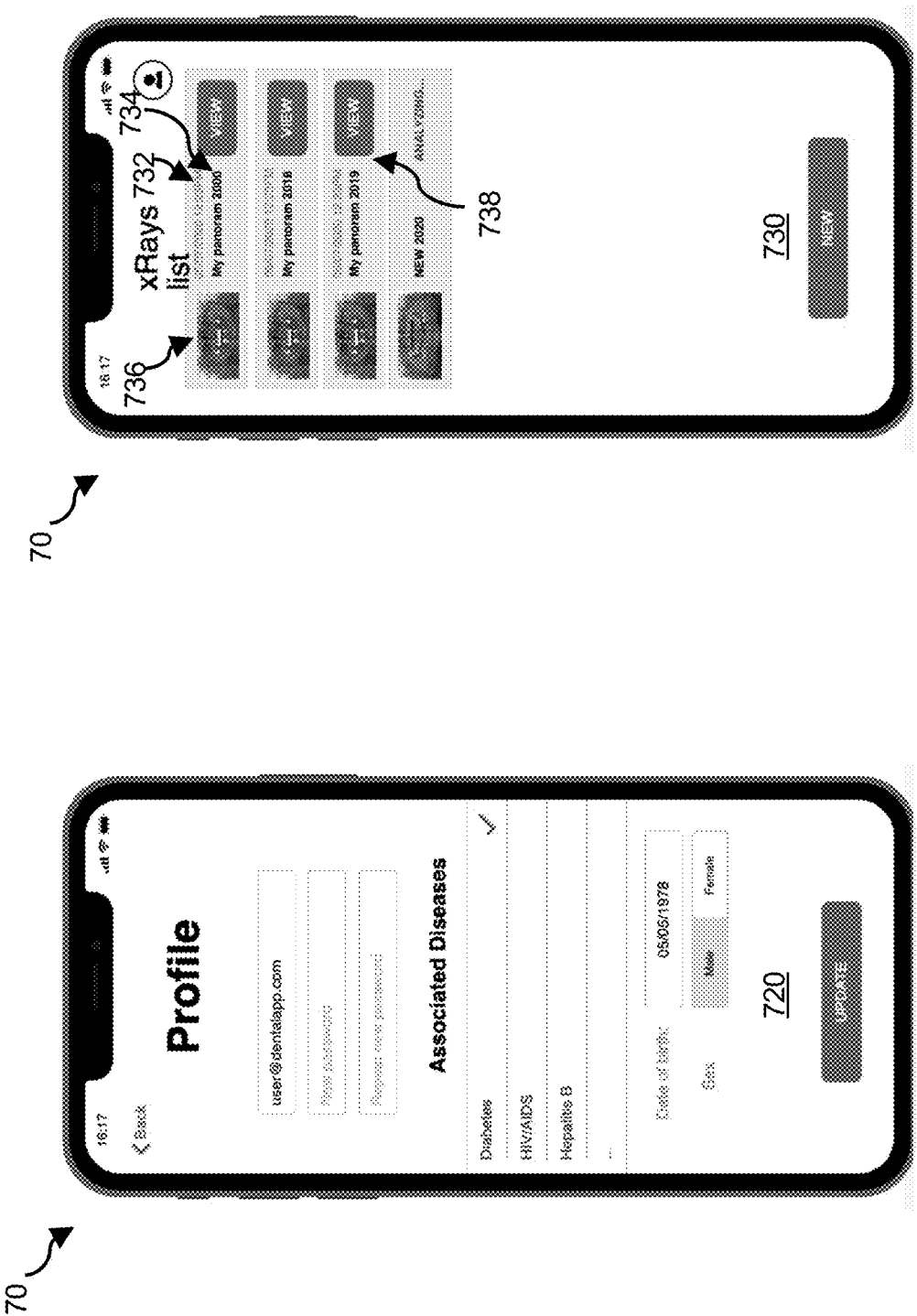

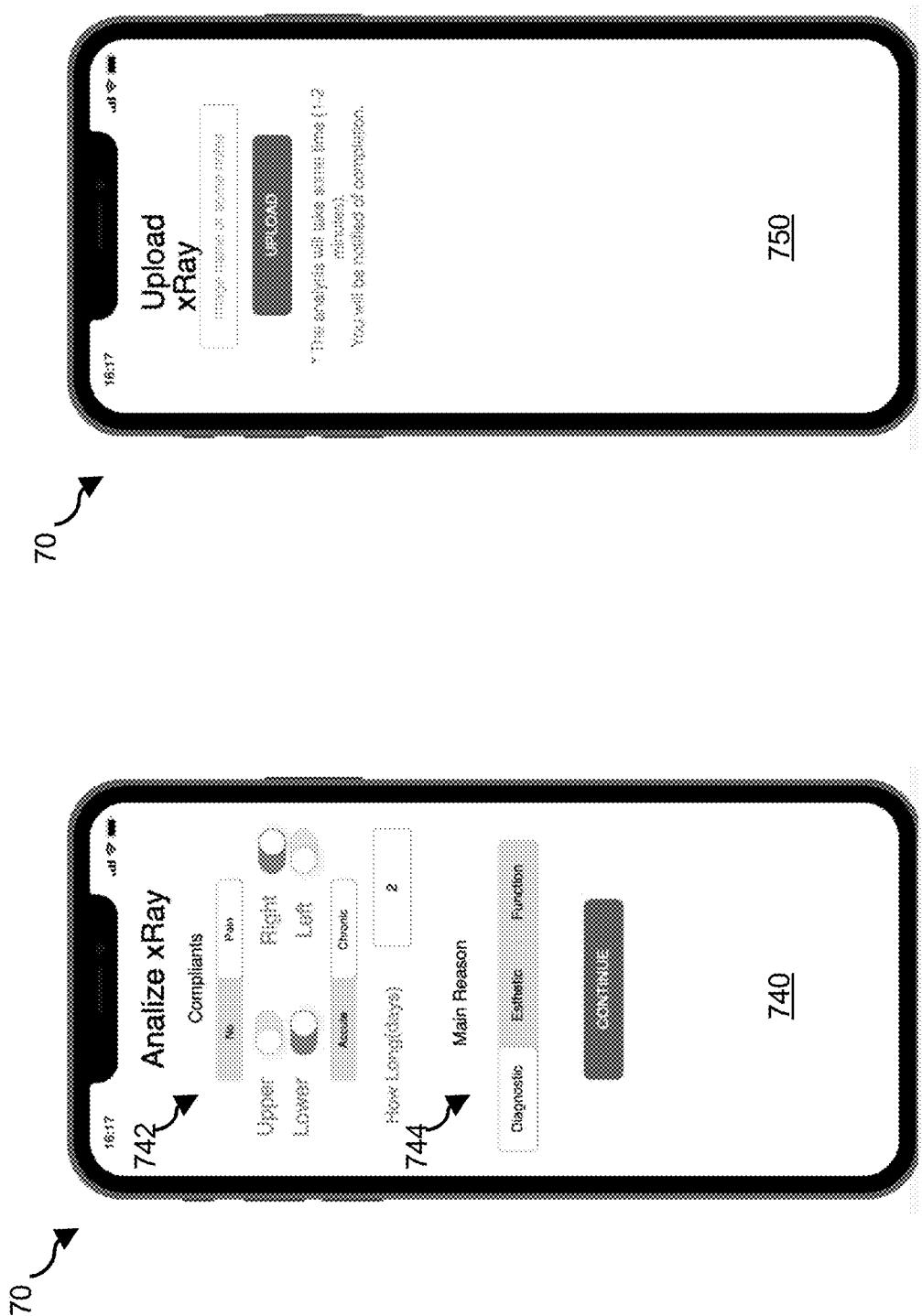

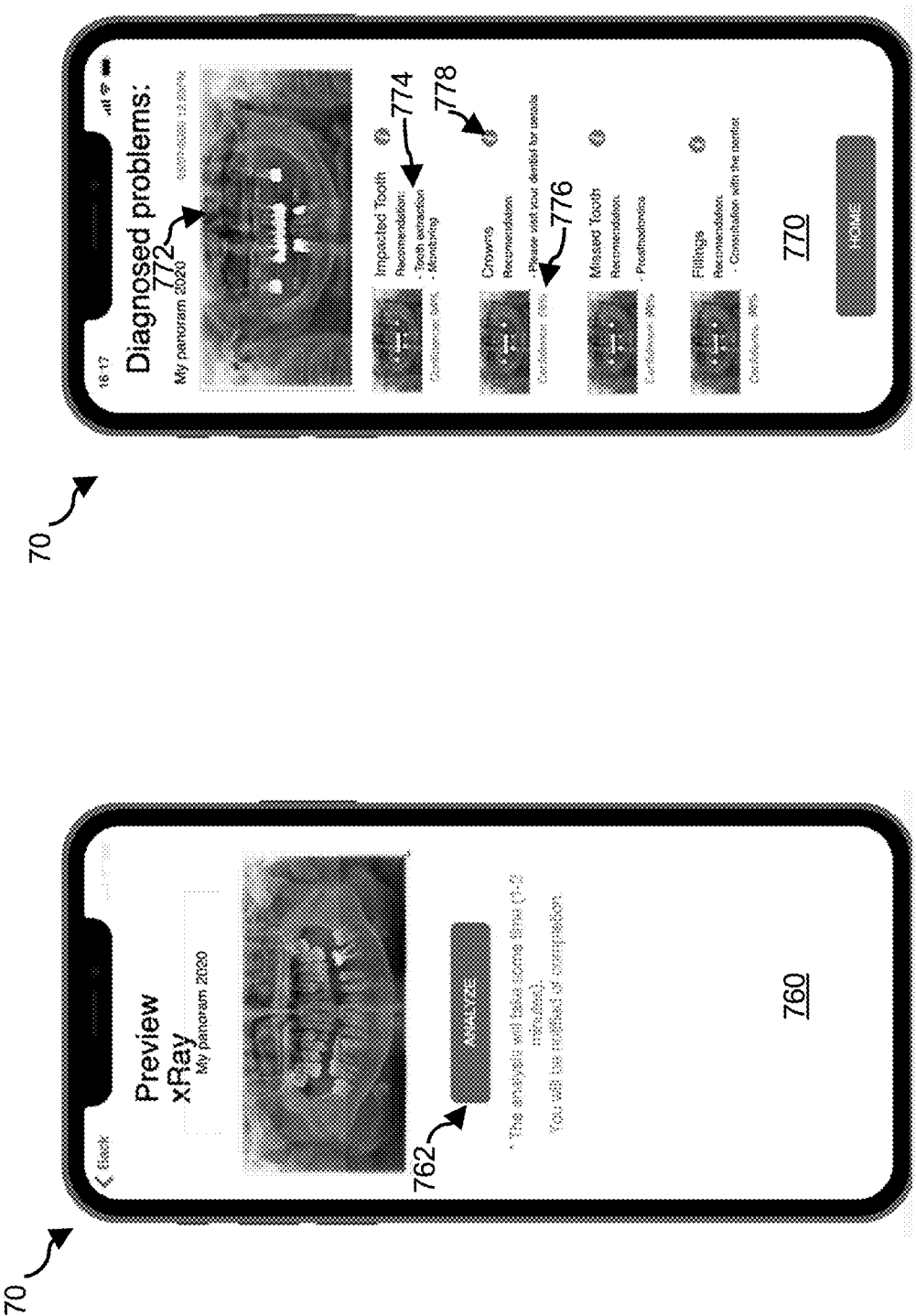

US 12,040,078 B2

DENTAL IMAGE ANALYSIS AND TREATMENT PLANNING USING AN ARTIFICIAL INTELLIGENCE ENGINE

CROSS-REFERENCE TO RELATED APPLICATIONS

This application claims priority to U.S. Provisional Application No. 62/931,498, titled "Dental Image Analysis and Treatment Planning Application," filed on Nov. 6, 2019, which is hereby incorporated by reference.

TECHNICAL FIELD

This application relates to automated dental image processing and analysis to provide automated outputs relating to a dental treatment plan.

BACKGROUND

Dental imaging such as X-ray imaging has been used to identify and diagnose various conditions that are presented by such images. Traditionally, a human practitioner would inspect and analyze patient images and make a determination of said conditions, recommending any necessary corrective actions. For the sake of increased clinical profit, patient expediency, and efficiency, some radiology and dentistry service providers have taken to outsourcing image analysis to achieve greater throughput. More recently, automated (computerized) image processing has become available in some contexts. A specially-programmed computer can automatically identify or classify certain medical or dental conditions based on input images of a patient. These techniques remain imperfect and are limited to expensive professional tools only available to subscribing clinics.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An embodiment is directed to a non-transitory computer-readable medium storing instructions that, when executed by a computer having a hardware-based processor, cause the computer to store a subject's dental images in a memory of the computer; automatically determine an apparent dental condition in the subject by analyzing the subject's dental images with an artificial neural network stored in the memory, the artificial neural network trained using manually-diagnosed dental images from other subjects; generate at least one output signal that represents the apparent dental condition; and generate a graphical output a representation of the apparent dental condition with respect to one of said dental images.

An embodiment is directed to a non-transitory computer-readable medium storing instructions that, when executed by a computer having a hardware-based processor, cause the computer to transmit a subject's dental images to a server having an artificial neural network stored in a memory of the server, the artificial neural network trained using manually-diagnosed dental images from other subjects; display a dental survey on a computer display of the computer; receive a subject's dental survey responses to the dental survey; transmit the subject's dental survey responses to the server; receive an output signal from the server, the output signal corresponding to an apparent dental condition in the subject; and display the apparent dental condition on the computer display.

And an embodiment is directed to computer-implemented method for automatically analyzing dental data for an apparent dental condition, comprising storing a plurality of manually-diagnosed dental images in a memory of a computer associated with an artificial neural network; mapping each manually-diagnosed dental image to at least one confirmed dental condition; storing a plurality of model dental survey response sets in the memory, each model dental survey response set corresponding to at least one model dental condition; and training the artificial neural network using the manually-diagnosed dental images, the mapping of each manually-diagnosed dental image to the at least one confirmed dental condition, and the model dental survey response sets.

BRIEF DESCRIPTION OF THE DRAWINGS

For a fuller understanding of the nature and advantages of the present concepts, reference is made to the detailed description of preferred embodiments and the accompanying drawings.

FIGS. 7A-I illustrate representative screenshots of a dental recommendation app according to an embodiment.

DETAILED DESCRIPTION

An artificial intelligence engine on a computer is trained using manually-diagnosed dental images from one or more patients. The dental images can include X-ray images such as panoramic X-rays, bitewing X-rays, periapical X-rays, and/or other dental X-rays. The dental images are manually diagnosed as having (or not having) one or more dental conditions. Examples of the dental conditions include cavities (e.g., tooth decay), periodontal disease, broken crowns, broken or cracked teeth, tooth erosion, broken or cracked fillings, bone loss, tooth misalignment (e.g., orthodontic condition), and/or other dental conditions.

The artificial intelligence engine can be further trained using dental survey response sets that correspond to one or more dental conditions. The dental survey response sets can be model dental survey response sets from hypothetical patients and/or actual dental survey response sets from actual patients.

The trained artificial intelligence agent can be used to predict or recommend whether the dental data for a subject (e.g., the subject's dental images and/or the subject's dental survey responses) indicate that he/she has one or more apparent dental conditions. This may be useful for a subject and/or a dental professional who would like a second opinion.

The trained artificial intelligence agent can be further programmed and/or trained to annotate the subject's dental images to indicate one or more features, such as landmark structures (e.g., jaw bone) and the tooth or teeth having the apparent dental condition(s).

A dental recommendation app on a client computer can be used to communicate with the artificial intelligence engine. For example, the dental recommendation app can be used to send the subject's dental images to the artificial intelligence engine. In addition, the dental recommendation app can be used to receive and display the annotated dental images. The dental recommendation app can also be used to receive and/or display dental information that describes the apparent dental condition(s), a list of dental professionals that can treat each apparent dental condition, and/or a cost estimate for treating each apparent dental condition.

Figure 1:
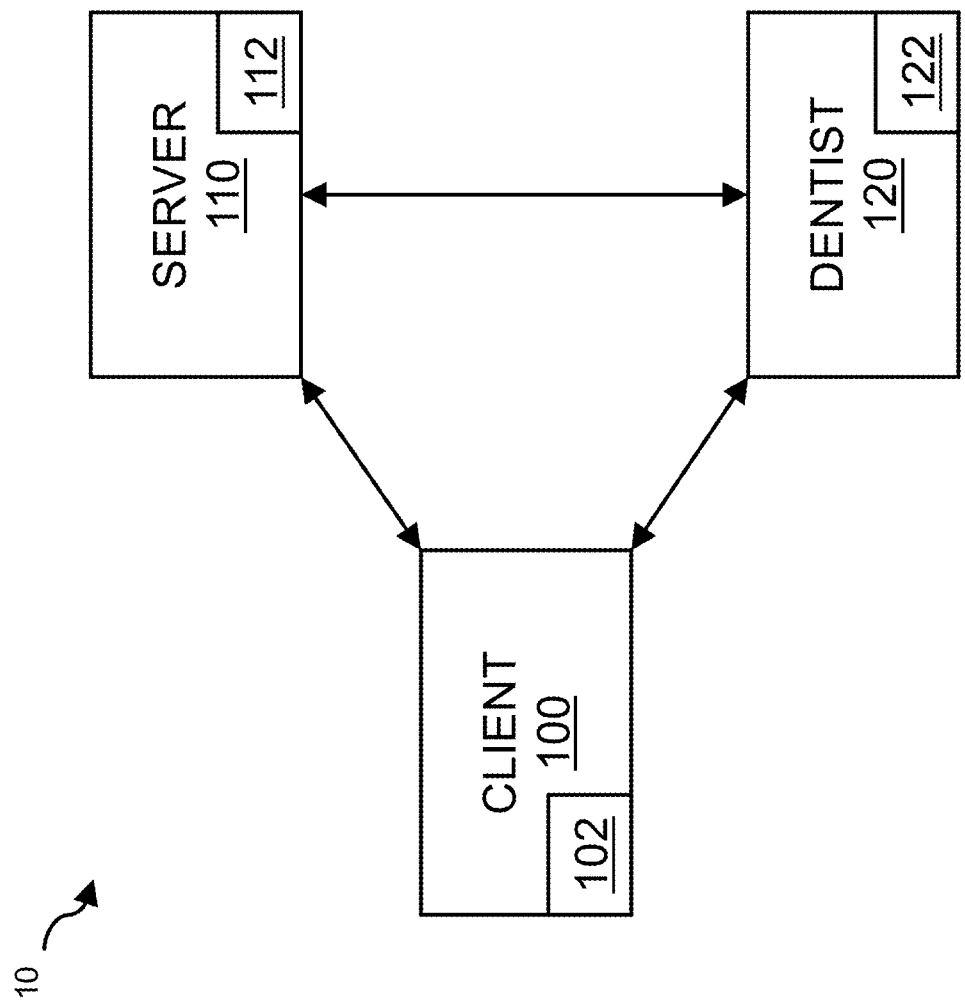
FIG. 1 is a block diagram of an architecture according to an embodiment.

FIG. 1 is a block diagram of an architecture 10 according to an embodiment. The architecture 10 includes a client computer 100, a server 110, and a dentist computer 120. The client computer 100 is in network communication with the server 110 and the dentist computer 120. The network communication can be implemented via a computer network that can include wired and/or wireless communication links, including but not limited to a local area network, a wide area network, and/or a virtual network. The computer network can further be implemented over the internet, the world wide web, a private network, a public network, a cellular network, and/or another network.

The client computer 100 can comprise a mobile computer (e.g., a laptop, tablet, or smartphone) or a stationary computer (e.g., a desktop computer). The client computer 100 includes a hardware-based processor, memory, a network interface, and peripherals such as a display, a keyboard, and/or a mouse. In some embodiments, the display is a touch screen in which case the keyboard and/or the mouse can be optional. The processor can execute or run software stored in the memory of the client compute 100r. The software can be stored in the memory as computer-executable instructions. The software can include a dental recommendation application (or "app") 102.

The server 110 includes a hardware-based microprocessor, memory, and a network interface. The server processor can execute or run software stored in the memory of the server 110. The software can be stored in the memory as computer-executable instructions. The software can include an artificial intelligence engine 112. The artificial intelligence engine 112 can include an artificial neural network (ANN) (e.g., a convolutional neural network or CNN, such as ResNet-50), a computer neural network, machine learning, and/or other artificial intelligence. The artificial intelligence engine 112 can operate in conjunction with the dental recommendation app 102.

The server memory can also include patient data, instructions, and other information for interacting with the dental recommendation app 102. For example, the server memory can store one or more dental images of the user associated with the client computer 100. The dental images (e.g., dental image data) can be uploaded by the user (e.g., over a computer network) using the dental recommendation app 102. For example, the user can retrieve his/her dental images from his/her dental provider and then transmit them to the server 110. Additionally or alternatively, the dental images can be provided through a patient portal, email, electronic delivery, shared file repository, and/or other means.

The dental images can include X-rays such as panoramic X-rays, bitewing X-rays, periapical X-rays, and/or other X-rays. The dental images can also include computer tomography (CT) data and/or other image data. Optionally, the system and method can accept or require magnetic resonance imagery (MRI) or other laboratory or medical test results. The dental images can be in any format, including JPEG, TIFF, or other computer image file format.

The dental images can be stored on the dentist computer 120 along with his/her patient record (e.g., medical history, surgical history, etc.). In some embodiments, the dentist computer 120 can access a dental image database 122 on the memory of the dentist computer 120 or in the memory of another computer in network communication with the dentist computer 120. In either case, the dental images can be provided to the user on a non-transitory computer-readable storage medium (e.g., a flash memory USB drive, a diskette, a CD, a hard drive, etc.) and/or through a computer network. The computer network can include the internet, the world wide web, a private network, a public network, a wired network, a wireless network, and/or another network. Some or all of the patient record can also be provided to the user on a non-transitory computer-readable storage medium and/or through a computer network and stored on the server memory, as discussed above.

Figure 2:
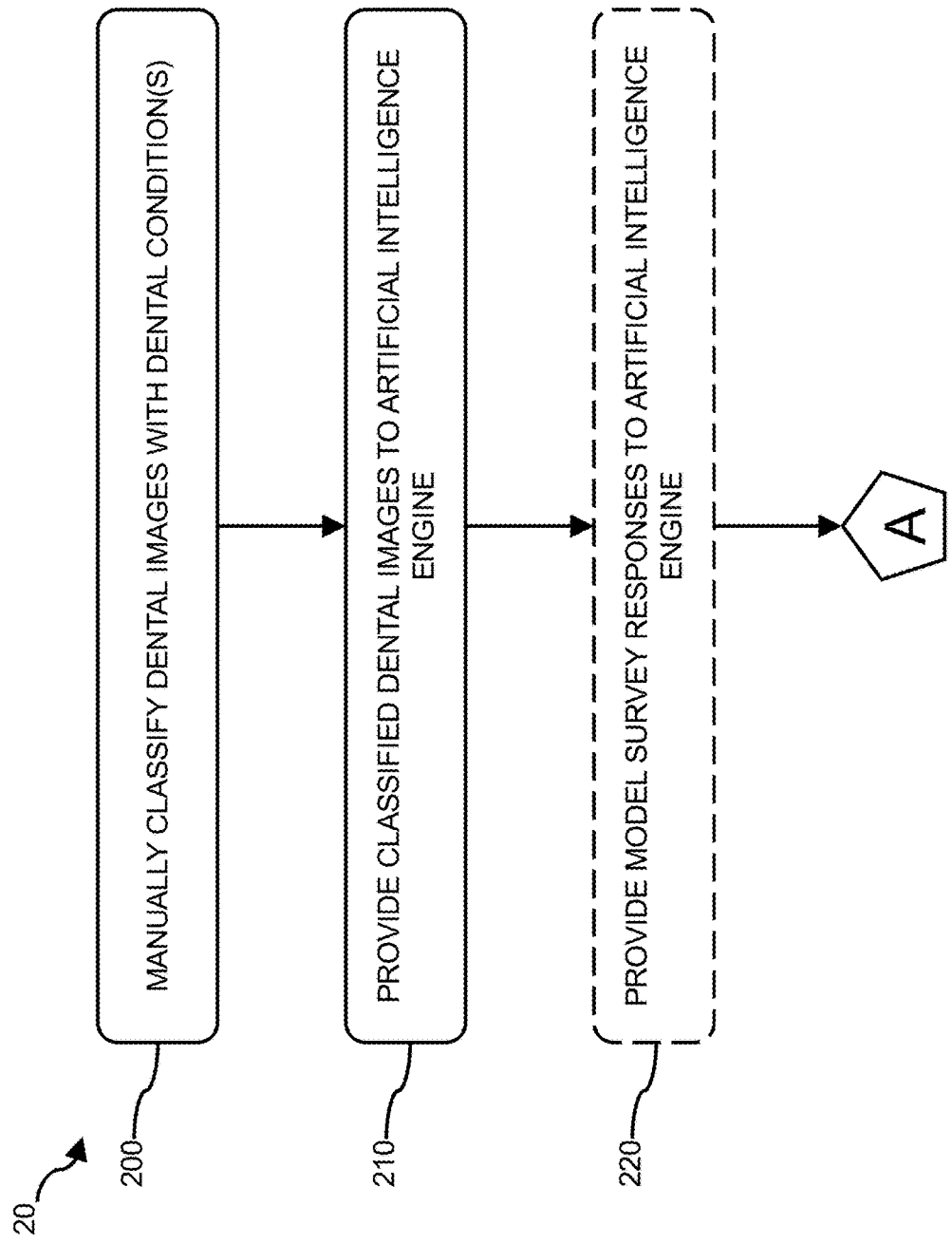
FIG. 2 is a flow chart of a method for training an artificial intelligence engine according to an embodiment.

FIG. 2 is a flow chart 20 of a method for training an artificial intelligence engine according to an embodiment. The method can be performed using some or all of architecture 10.

In step 200, a plurality of training dental images of model or existing subjects/patients are manually processed or classified by dental professionals (e.g., dentists, orthodontists, periodontists, etc.). Depending on the condition the training dental images can be classified according to the availability of predetermined dental conditions on the image or dental professionals can outline one or more dental conditions using special tools like Amazon SageMaker Ground Truth. After image processing is completed, the data is separated for each condition and stored in the special files with JSON formatting that can be further used to train machine learning algorithms, validate training results or review by specialists. The dental conditions can include cavities (e.g., tooth decay), periodontal disease, broken crowns, broken or cracked teeth, root canal, tooth erosion, broken or cracked fillings, bone loss, tooth misalignment (e.g., orthodontic condition), periapical abscess, implanted teeth, and/or other dental conditions. In some embodiments, each training dental image can be manually classified by a plurality (e.g., 2 or more, 3 or more, etc.) of dental professionals In step 210, the manually classified training dental images are provided to the artificial intelligence engine 112. The manually-classified training dental images can be provided to the artificial intelligence engine 112 by uploading them from a first computer to the server 110 using a computer network connection. Alternatively, the manually-classified training dental images can be provided to the server 110 prior to or concurrently with the manual classification step 200, in which case a mapping of each manually-classified training dental image to its respective dental condition(s) can be provided in step 210. A table or database can be used to map each manually-classified training dental image to its respective dental condition. In some embodiments, only the manually-classified training dental images that are unanimously classified by all dental professionals are provided to the artificial intelligence engine 112.

In some embodiments, the manually-classified training dental images can be artificially altered or manipulated to provided manipulated training dental images which can be provided to the artificial intelligence engine 112 in addition to the manually-classified training dental images discussed above. The manipulated training dental images can represent the normal visual range of variations of the dental condition(s) in each dental image. Additionally or alternatively, the manipulated training images can be rotated, stretched along an axis, or otherwise image processed, which can improve the sensitivity of the artificial intelligence engine 112.

The manually-classified training dental images can also include markings, mappings, or other data that indicate the location of one or more dental landmarks in each manually-classified training dental image. The dental landmarks can include the jaw bone, the number of each tooth, the TMJ, and/or other dental landmarks.

In optional step 220, model response sets to a dental survey or questionnaire are provided to the artificial intelligence engine 112. Each set of model dental survey responses can correspond to at least one model dental condition. For example, a first set of model dental survey responses can correspond to the dental condition of cavities. A second set of model dental survey responses can correspond to the dental condition of periodontal disease. And so on. Additionally or alternatively, each set of model dental survey responses can correspond to a respective manually-classified dental image (or set of manually-classified dental images). In some embodiments, one or more sets of model dental survey responses can correspond to a plurality of concurrent dental conditions (e.g., cavities and periodontal disease).

In some embodiments, variations of one or more sets of model dental survey responses can be provided to account for the normal range of responses encountered by dental professionals. For example, a patient with a cavity may or may not experience tooth sensitivity. To account for this variation, one set of model dental survey responses can include a negative response to a question regarding whether the patient is experiencing any tooth sensitivity, and another set of model dental survey responses can include a positive response to this question. Additional examples will be apparent to those of ordinary skill in the art.

The model dental survey responses can represent actual dental survey responses from existing or past patients (e.g., patients other than the subject) that have the dental condition(s) and/or hypothetical responses from hypothetical patients that have the dental condition(s).

In step 230, the artificial intelligence engine 112 is trained using the manually classified training dental images, data generated by dental professionals on step 200 and the model dental survey responses. The data from step 200 is divided into 2 parts, a training part and a validation part. The validation is used in the quality control of the model's prediction. Then, the prediction models for each dental condition are trained, e.g. by sending to the input id convolutional neural network (like ResNet-50) batches of images and monitor the prediction quality of the network using validation data from step 200.

For each training job before the start, hyperparameters are chosen, e.g., special parameters of the learning algorithm used to improve prediction quality, which in some examples may include one or more of: Kernel size or size of a filter; kernel type values of the actual filter (e.g., edge detection, sharpen); stride or the rate at which the kernel passes over the input image; padding—add layers of zeros so that the kernel passes over the edge of the image; Hidden layer count or number of layers between input and output layers; activation functions to allow the model to learn nonlinear prediction boundaries; learning rate that regulates the update of the weight at the end of each batch; momentum, which regulates the value to let the previous update influence the current weight update; the number of epochs—the iterations of the entire training dataset to the network during training; and the batch size, i.e., the number of patterns shown to the network before the weights are updated.

This process can be applied for the predetermined count of iterations or stopped earlier based on validation metrics values, to prevent over-learning of the model. The artificial intelligence engine 112 can also be trained using manipulated training dental images. In some embodiments, the model dental survey responses are optional.

In step 240, the artificial intelligence engine 112 is tested using a validation set of test dental images, data generated by dental professionals at step 200 and one or more respective test dental survey response sets. The output of each test (e.g., dental test image(s) and respective dental survey response set) is evaluated in step 250. If the artificial intelligence engine 112 correctly interprets the tests (or a threshold percentage of the tests, such as 95% or more), the training is completed in step 260 otherwise the training process will be continued. This process can be repeated many times in order to improve the efficiency and accuracy of the results, by adding more input data for the training or by using additional algorithms to tune optimal hyperparameters (e.g. Bayesian algorithm) for each condition and input data prepared by those skilled in the art. In some embodiments, re-training can include adjusting one or more parameters of the artificial intelligence engine 112 to improve its accuracy. This loop is repeated until the artificial intelligence engine 112 correctly interprets the tests (or a threshold percentage of the tests) in step 250 at which point the training is completed in step 260.

Figure 3:
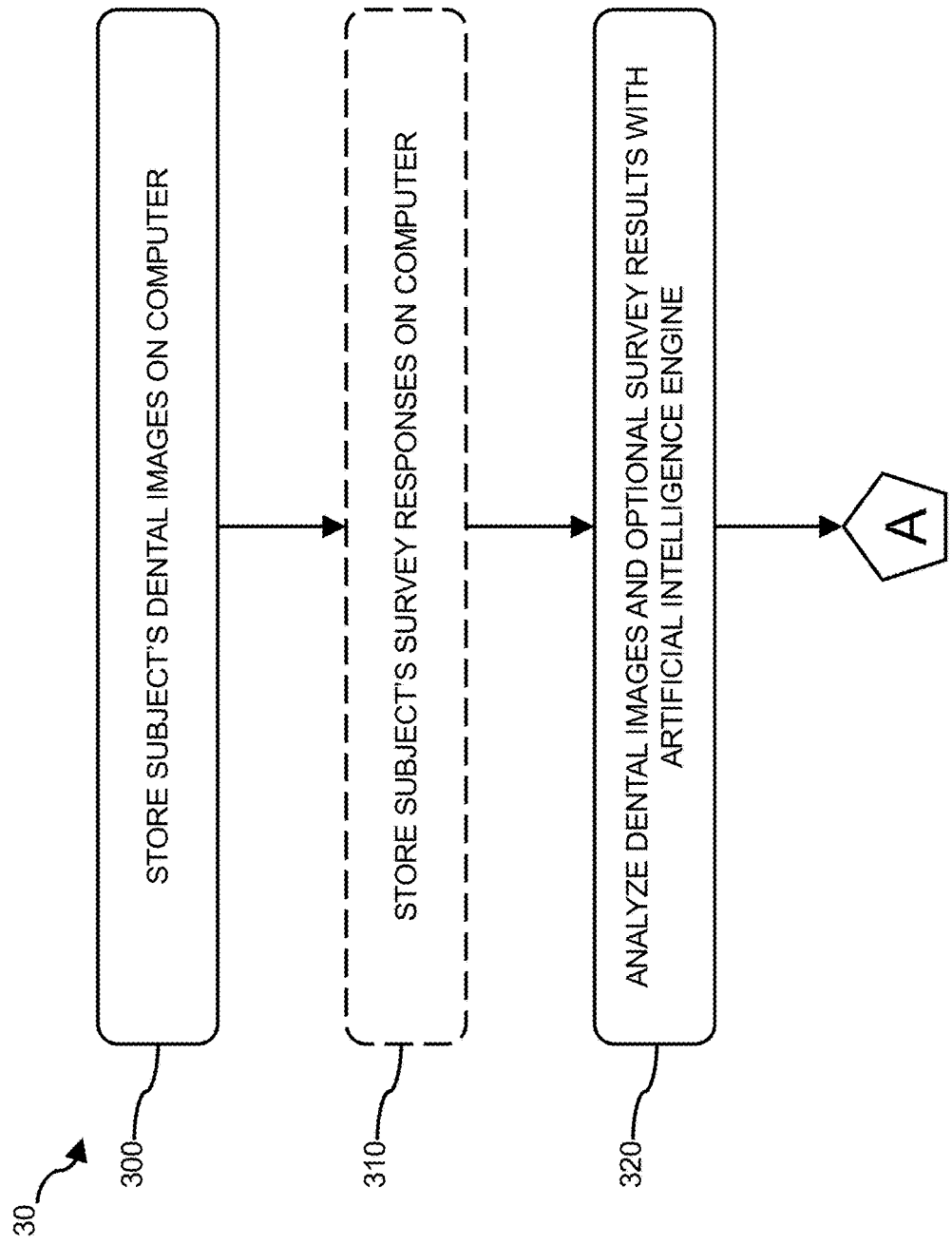
FIG. 3 is a flow chart of a method for providing a dental condition recommendation according to an embodiment.

FIG. 3 is a flow chart 30 of a method for providing a dental condition recommendation according to an embodiment. The method can be performed using some or all of architecture 10.

In step 300, one or more dental images from a subject are stored on a computer. For example, the subject's dental images can be stored on the memory of server 110 or a memory operatively coupled to server 110. The subject's dental images can be uploaded to the server 110 by the subject (e.g., using the dental recommendation app 102), by the dental provider (e.g., using dentist computer 120), or by another person or entity (e.g., by a dental insurance company).

In optional step 310, the subject's dental survey responses are stored on the computer. For example, the subject's dental survey responses can be stored on the memory of server 110 or a memory operatively coupled to server 110. The subject's dental survey responses can be uploaded to the server 110 by the subject (e.g., using the dental recommendation app 102), by the dental provider (e.g., using dentist computer 120), or by another person or entity (e.g., by a dental insurance company). In some embodiments, the computer (e.g., server 110) sends a dental survey in response to the receipt of the subject's dental images. Alternatively, the computer can provide the dental survey to the subject via the dental recommendation app 102 prior to or concurrently with receiving the subject's dental images.

In step 320, the trained artificial intelligence engine 112 analyzes the subject's dental image(s) and the optional dental survey responses stored in steps 300 and 310, respectively. Whole or partial image recognition can be implemented as well as image comparison, which comprises routines for analyzing and classifying features of a subject's dental image(s) using the training dental images of known and classified images.

In step 330, the trained artificial intelligence engine 112 generates an output signal that corresponds to one or more apparent dental conditions and an indication of the tooth or teeth having the apparent dental condition(s). The apparent dental condition(s) can provide an independent evaluation of the subject's dental health (e.g., using the subject's dental image(s) and survey results) to supplement a dental professional's diagnosis, such as for a second opinion. In some embodiment, the trained artificial intelligence engine 112 generates an output signal that represents the likelihood or probability that the subject has each apparent dental condition. The likelihood or probability can be represented qualitatively or quantitatively. A qualitative likelihood or probability can be represented as (a) high, medium, or low, (b) corresponding to the number of an object displayed (e.g., 3 out of 5 stars/teeth/another object), (c) color or color shading, or (d) another qualitative representation. A quantitative likelihood or probability score can be represented as a decimal, fraction, or percentage where the likelihood/probability is in the range of 0 to 1, where 0 indicates there is no likelihood/probability of the apparent dental condition and 1 indicates there is high confidence of the apparent dental condition. In either case, the likelihood or probability can be determined based on a fit of the actual subject dental data (e.g., the subject's dental images and, optionally, the subject's dental survey responses) with the model or training set of dental data (e.g., the training dental images and, optionally, the training dental survey responses).

In some embodiments, the trained artificial intelligence engine 112 only determines that the subject has an apparent dental condition when the likelihood or probability score is greater than a threshold amount. For example, when the likelihood/probability score is quantitative, the threshold amount can be 70% or more, 75% or more, or 80% or more. When the likelihood/probability score is below the threshold, the trained artificial intelligence engine 112 does not indicate that the subject has an apparent dental condition.

In step 340, the server 110 generates annotations of the subject's dental image(s) to illustrate the apparent dental condition(s). The annotations can include marking the tooth or teeth having the apparent dental condition(s) and/or marking the portion of the tooth or teeth having the apparent dental condition(s). The annotations can also include anatomical structures or landmarks, such as the patient's jaw line, temporomandibular joint (TMJ), outlines of teeth, gum line, and/or other anatomical structures. Additionally or alternatively, the annotations can be provided in a graphic illustration of representative or model teeth.

In step 350, the server 110 provides dental information (e.g., using a dental information output signal) relating to the apparent dental condition(s). The dental information can include a medical definition of each apparent dental condition. The dental information can also include common causes of each apparent dental condition, common symptoms (if any) of each apparent dental condition, and/or common treatments for each apparent dental condition. The server 110 can provide some or all of the dental information in step 350 automatically and/or in response to a request from the dental recommendation app 102 (e.g., based on user input). The dental recommendation app 102 can display some or all of the dental information automatically and/or in response to user input (e.g., clicking on a link associated with an annotated dental image).

In step 360, the server 110 provides a cost estimate (e.g., in a cost estimate output signal) for treating each apparent dental condition. The cost estimate can be based on the subject's location, the subject's medical history and/or dental history, and/or other factors. The server 110 can provide the cost estimate in step 360 automatically and/or in response to a request from the dental recommendation app 102 (e.g., based on user input). The dental recommendation app 102 can display some or all of the cost estimate automatically and/or in response to user input (e.g., clicking on a link associated with an annotated dental image). In some embodiments, the server 110 can provide, and the dental recommendation app 102 can display, a list of dental providers that can treat the apparent dental condition(s) that are located within a predetermined geographical range of the subject.

Figure 4:
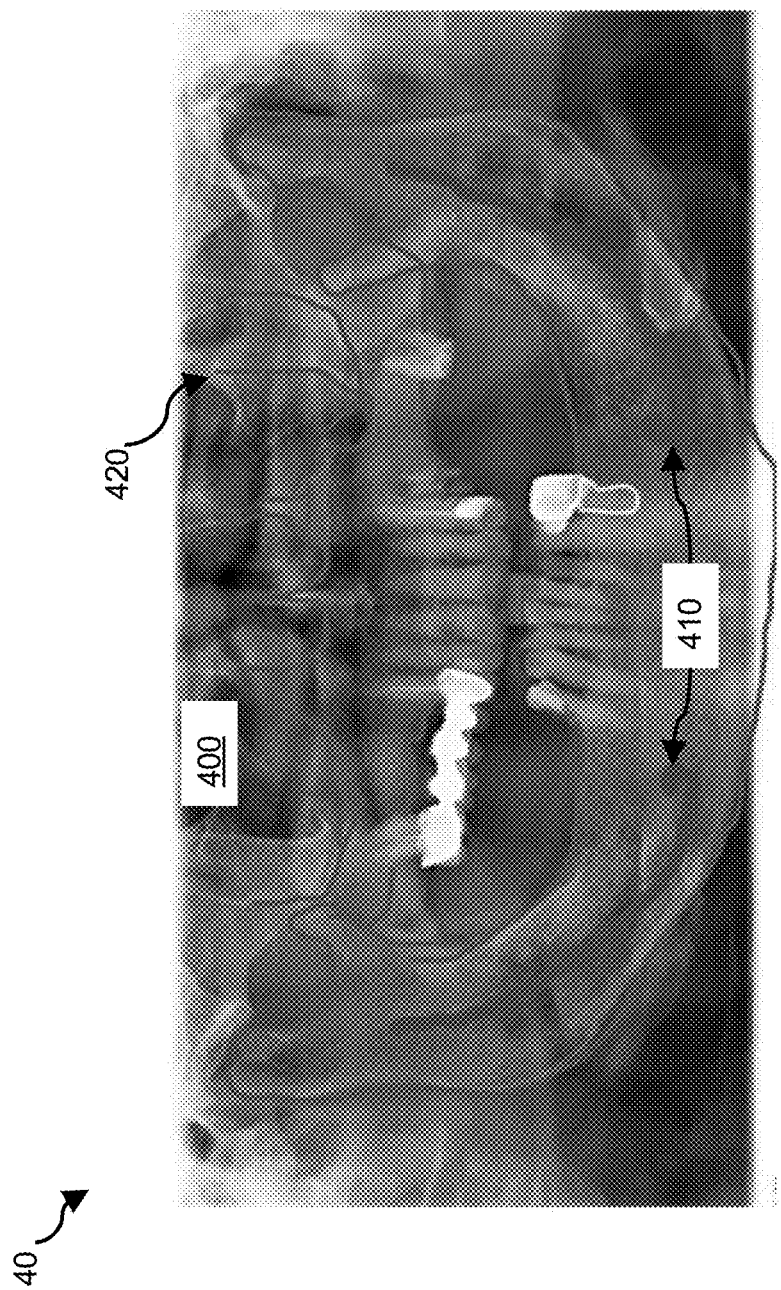
FIGS. 4 and 5 illustrates example annotated dental images according to an embodiment.

FIG. 4 illustrates a first example annotated X-ray image 40 of a subject's jaw and teeth according to an embodiment. The annotated X-ray image 40 can be generated in step 340. The annotated X-ray image 40 includes the original X-ray image 400 (e.g., a panoramic X-ray image) provided by the subject and annotations 410 (mandibular nerve), 420 that are overlaid on the original X-ray image 400. The annotation 410 indicates the jaw structure and the annotation 420 indicates the TMJ. The example shows a breach near the upper left and a crown and broken tooth. In other embodiments, the annotations 410 and/or 420 can include text, color, shading, or other visual features.

Figure 5:
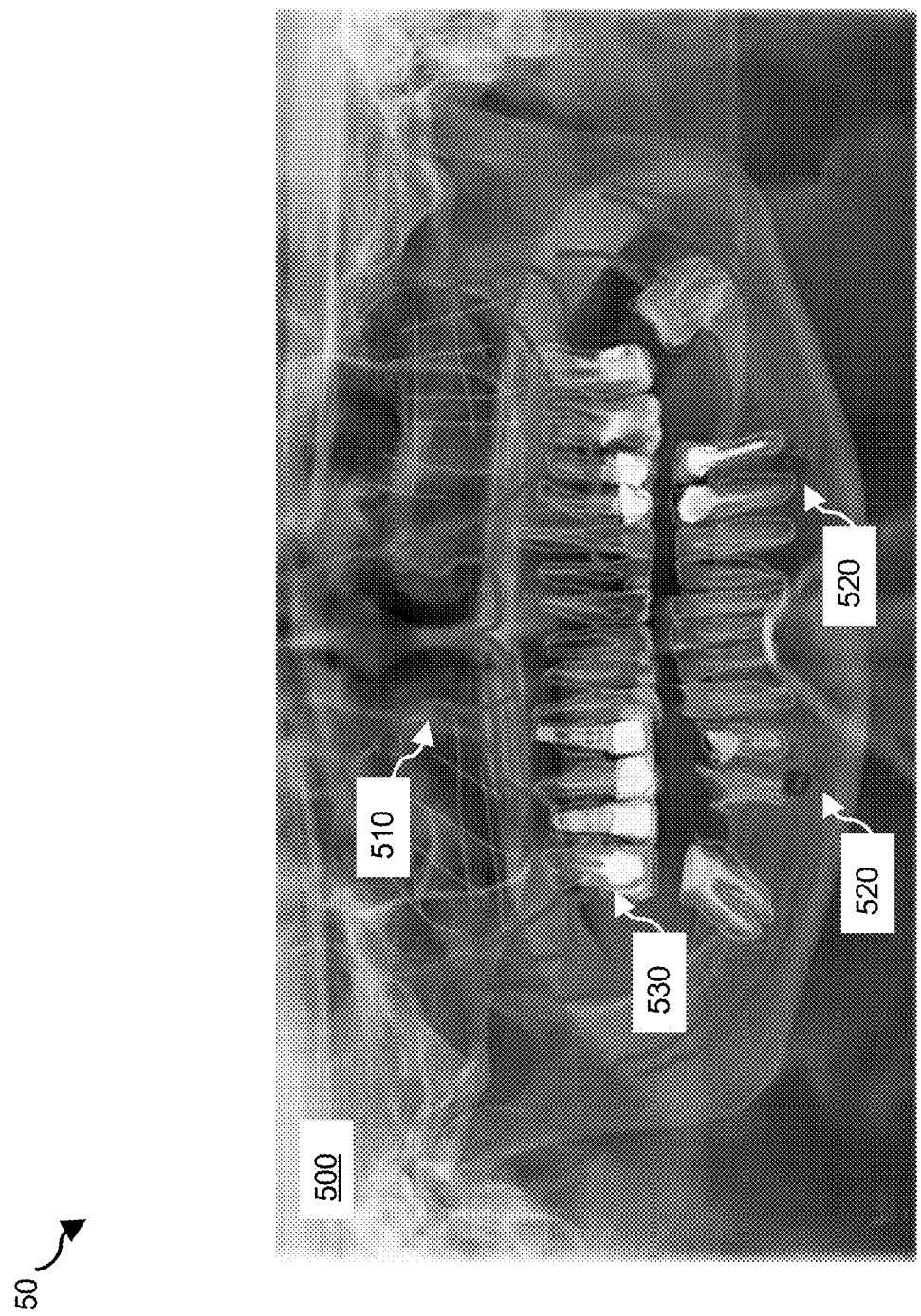

FIG. 5 illustrates a second example annotated panoramic X-ray image 50 of a subject's jaw and teeth according to an embodiment. The annotated X-ray image 50 can be generated in step 340. The annotated X-ray image 50 includes the original X-ray image 500 provided by the subject and annotations 510, 520, 530 that are overlaid on the original X-ray image 500. The annotation 510 indicates the jaw structure, the annotation 520 indicates the TMJ, and the annotation 530 indicates a recommended tooth to be extracted. In other embodiments, the annotations 510, 520, and/or 530 can include text, color, shading, or other visual features.

Figure 6:
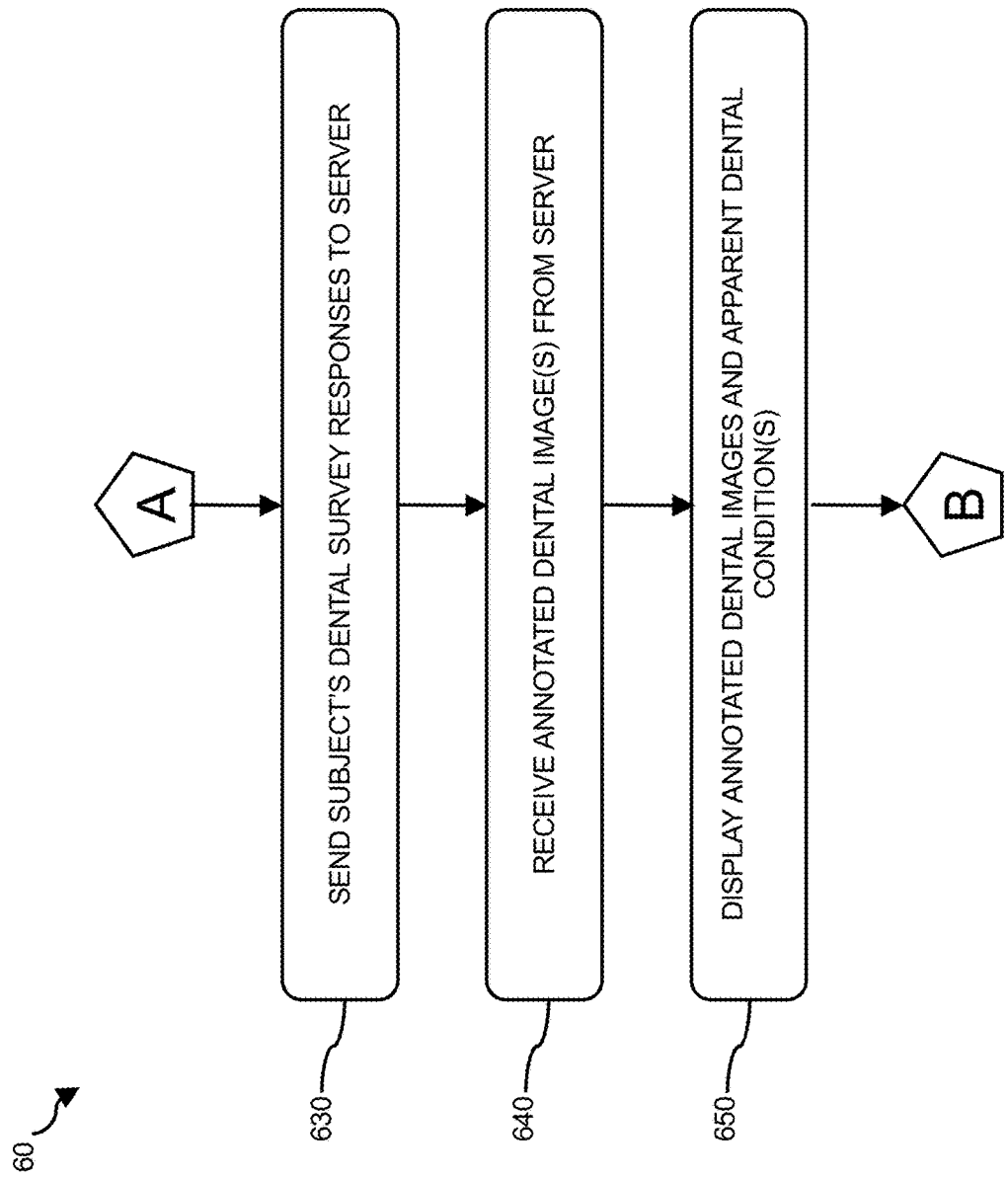
FIG. 6 is a flow chart of a method for requesting a recommendation of an apparent dental condition according to an embodiment.
Figure 6:
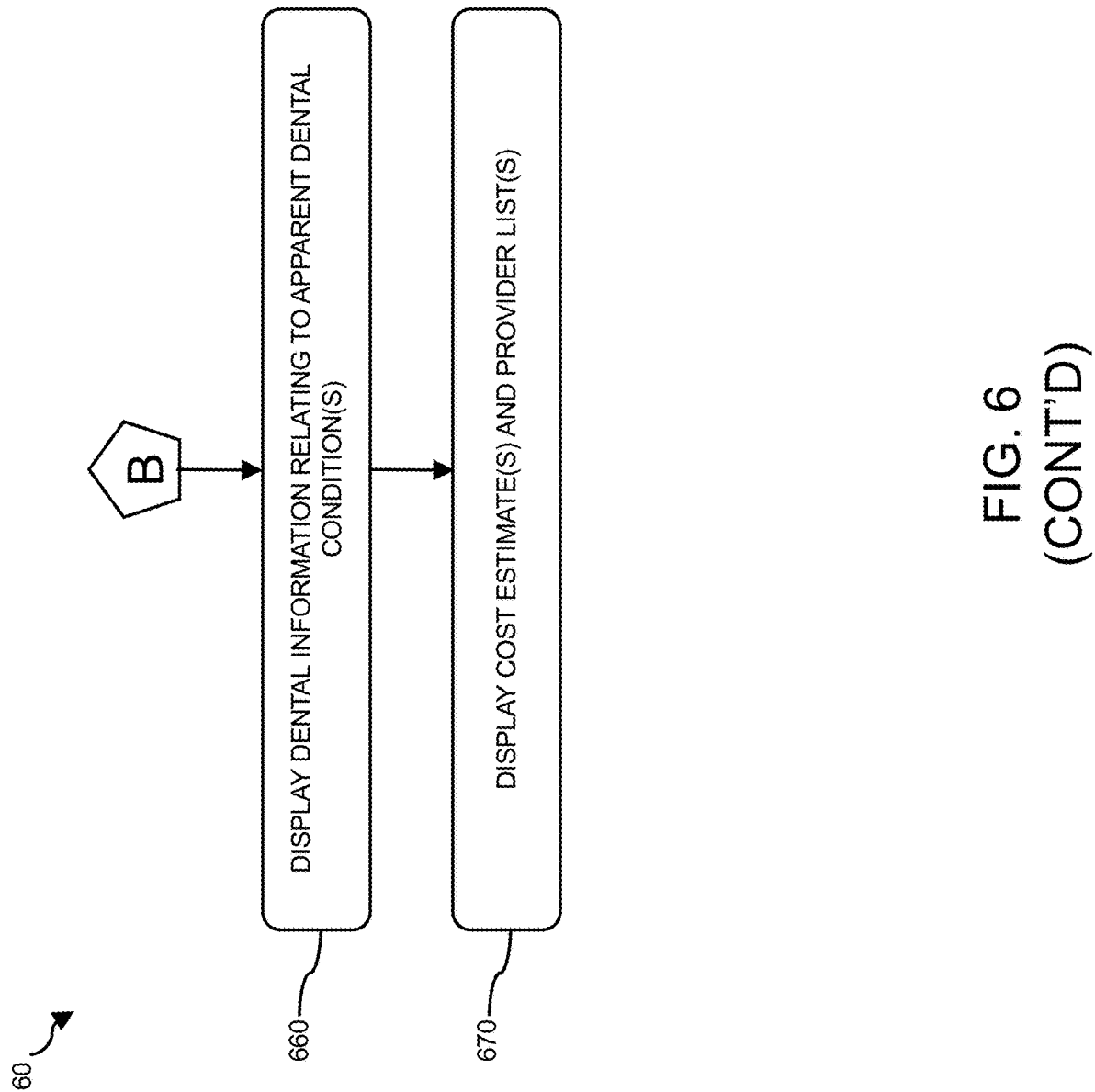

FIG. 6 is a flow chart 60 of a method for requesting a recommendation of an apparent dental condition according to an embodiment. The method can be performed using some or all of architecture 10.

In step 600, the subject sends his/her dental images to the server 110. The subject can send the dental images to the server 110 using the dental recommendation app 102 and/or through another application on the client computer 100. Additionally or alternatively, the dental images can be sent using the dentist computer 120.

In step 610, the subject's dental history is optionally sent to the server 110. The subject's dental history can include narratives, diagnosis codes, tooth charts, surgical histories, and/or other dental history information. The subject's medical history (e.g., height, weight, past medical issues and treatments, and/or other medical history) can also be provided in 610. The subject can send his/her dental history to the server 110 using the dental recommendation app 102 and/or through another application on the client computer 100. Additionally or alternatively, the dental history can be sent using the dentist computer 120.

In step 620, the client computer 100 (e.g., the dental recommendation app 102) receives responses to a dental survey. The dental survey can be answered using the dental recommendation app 102. In some embodiments, the dental survey is pre-stored on the client computer 100 (e.g., as part of the dental recommendation app 102). Alternatively, the dental survey can be sent from the server 110 to the client computer 100 (e.g., in response to a request from the dental recommendation app 102).

In step 630 (via placeholder A), the client computer 100 (e.g., the dental recommendation app 102) sends the dental survey responses to the server 110. In some embodiments, steps 620 and 630 are optional.

In step 640, the client computer 100 (e.g., the dental recommendation app 102) receives one or more annotated dental images from the server 110. The server 110 can generate the annotated dental images according to step 340, as discussed above. Alternatively, the dental recommendation app 102 can receive one or more layers of annotations (e.g., from server 110) that are overlaid over the original dental images to form the annotated dental images.

In step 650, the client computer 100 (e.g., the dental recommendation app 102) displays the annotated dental image(s) received in step 640 and the subject's apparent dental condition(s) in a display of the client computer 100. The subject's apparent dental condition(s) is/are provided by the server 110, for example in response to a request by the client computer 100 for the server 110 to analyze the subject's dental image(s) and his/her optional dental survey responses. The client computer 100 can also receive, in an output signal (e.g., a likelihood output signal) from the server 110, a likelihood or probability that the subject has each apparent dental condition. The likelihood or probability can be represented qualitatively or quantitatively, as discussed above. The client computer 100 can display the likelihood/probability graphically and/or textually on a display of the client computer 100.

In step 660, the client computer 100 (e.g., the dental recommendation app 102) displays dental information relating to the apparent dental condition(s) displayed in step 650. The dental information displayed in step 660 can be the same as the dental information provided by the server 110 in step 350.

In step 670, the client computer 100 (e.g., the dental recommendation app 102) displays a cost estimate (or cost estimate range) for each apparent dental condition displayed in step 650. The cost estimate(s) displayed in step 670 can be the same as the cost estimate(s) provided by the server 110 in step 360. In addition, the client computer 100 (e.g., the dental recommendation app 102) can display a list of providers to provide treatment for each apparent dental condition displayed in step 650.

Embodiments of the invention can be provided to users in a tiered service model, e.g., a minimal, a standard or a complete level of functionality and service. The user can therefore elect from a plurality of levels or degrees of dental work desired, needed or as can be afforded.

As an example, in a minimal service tier, embodiments of the invention can provide for analysis and recommendations for endodontic treatment of the 6, 7, 12, 13 and 14 teeth and/or regarding filling or restoration of the 3, 6, 7, 8, 9 12, and 14 teeth. An example standard service tier can provide for analysis and recommendations for endodontic treatment of the 6, 7, 12 and 14 teeth as before, extraction of the 1 and 16 teeth, filling/restoration of the 3, 6, 7, 8 and 12 teeth, and crown/bridge restoration of the 3, 4, 12, 13 and 14 teeth. An example complete service tier can provide for analysis and recommendations regarding the issues raised above in the standard tier but also a cast post, crown of the 3, 4, 12 and 14 teeth, dental implantations of the 13, 19 and 30 teeth, and crown restoration of the 3, 4, 12, 13, 14, 19, 20, 29 and 30 teeth.

In another example, the user can be recommended to receive hygiene advice, to receive a night guard splint, to continue monitoring teeth 6, 7, 12, 13 and 14, and so on.

FIGS. 7A-I illustrate representative screenshots of a dental recommendation app 70 according to an embodiment. The dental recommendation app 70 can be the same as or different than dental recommendation app 102.

Figure 7B:
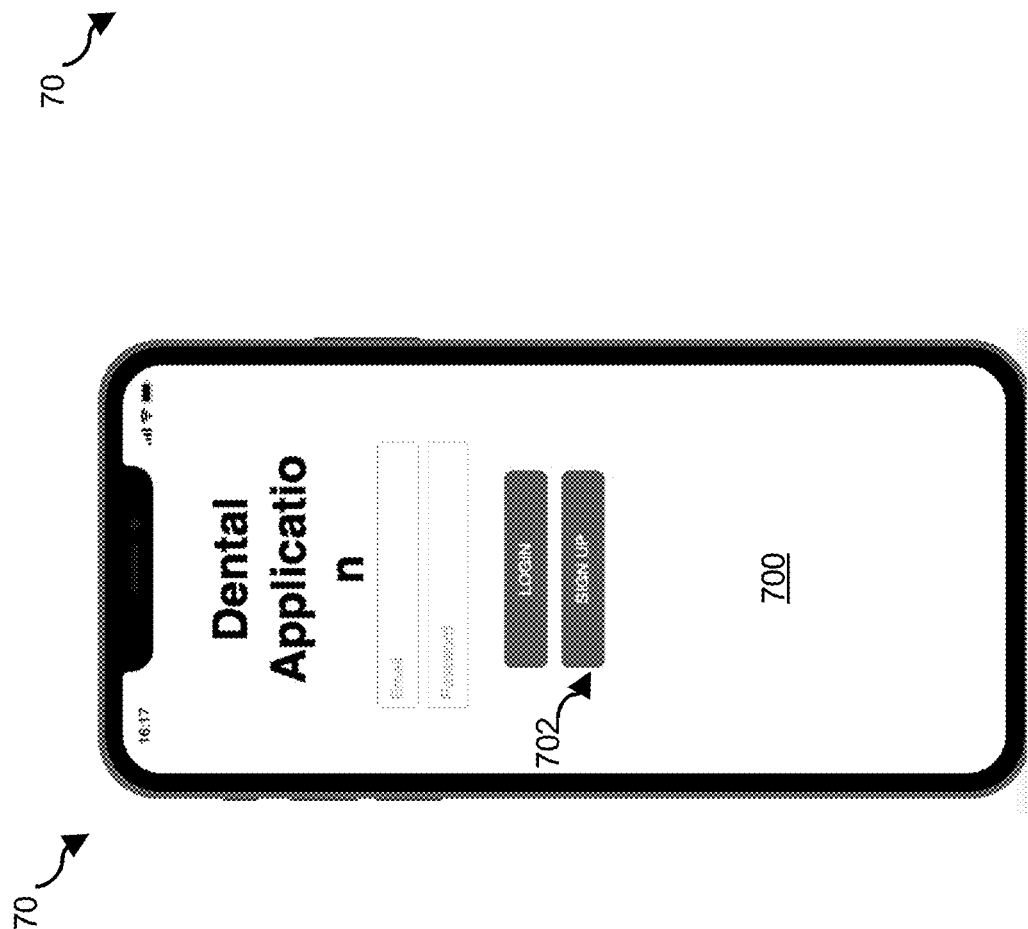
Figure 7A:
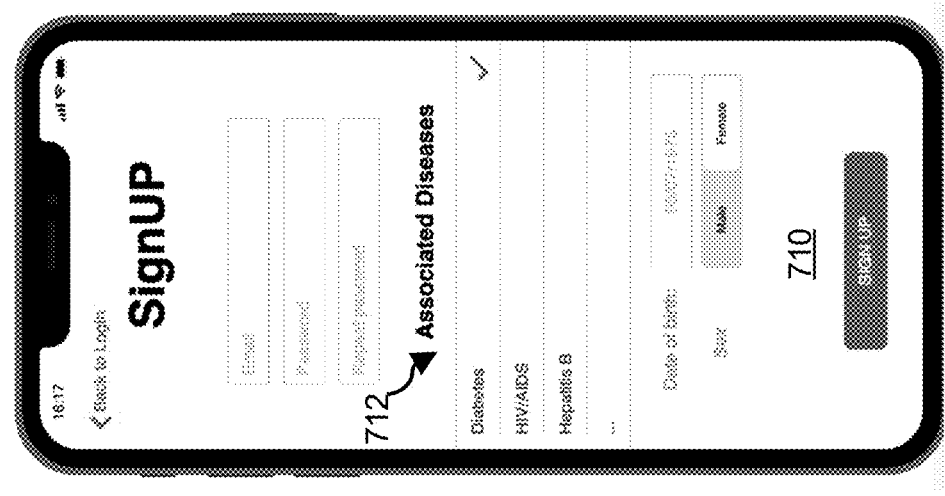

FIG. 7A illustrates a login screen 700 where the user can enter his/her credentials (e.g., email address and password) to access the dental recommendation app 70. First-time users can use the sign-up button 702 to register with the dental recommendation app 70.

FIG. 7B illustrates a registration screen 710 that can be displayed when the user presses the sign-up button 702 in FIG. 7A. The registration screen 710 includes patient health data fields 712 where the user can indicate whether he/she has any diagnosed medical diseases or conditions (e.g., diabetes, high blood pressure, etc.), his/her age (e.g., date of birth), gender, weight, and/or other patient health data. FIG. 7C illustrates a partially-filled out registration screen 720.

FIG. 7D illustrates a dental images screen 730 that includes a list of the user's dental images (e.g., X-rays). The dental images screen 730 can display metadata pm the user's dental images, such as the date and time 732 that each dental image was uploaded, the title 734 of each dental image (e.g., a user-created or an automatically-created title), and/or a thumbnail 736 of each dental image. Each thumbnail 736 can include annotations, if any, that the dental recommendation app 70 has made for that dental image. For example, the thumbnails 736 for titles 734 "My panoram 2000," "My panoram 2018," and "My panoram 2019" include annotations and a view button 738 to view the respective annotated dental image. The thumbnail 736 for title 734 "NEW 2020" does not include any annotations. Instead, the dental images screen 730 indicates that dental recommendation app 70 is analyzing the dental images for title 734 "NEW 2020."

FIG. 7E illustrates an X-ray analysis request screen 740 that includes complaint input fields 742 and X-ray analysis reason field 744. The complaint input fields 742 include a pain field to indicate whether the user is experiencing any pain. If the user is experiencing pain, the user can indicate (a) where he/she is experiencing the pain (e.g., left- or right-side, upper- or lower-teeth), (b) whether the pain is acute or chronic, and (c) how long he/she has been experiencing the pain. The X-ray analysis reason field 744 allows the user to select the main reason that he/she would like to have his/her dental images analyzed. The main reason may be diagnostic (e.g., to determine the source of the pain, or to determine if any cavities or other dental issues are present), aesthetic (e.g., to detect orthodontic issues), or functional (e.g., to determine if the patient's TMJ is aligned). The main reason can impact how the dental recommendation app 70 analyzes the patient's dental images.

After the user completes the X-ray analysis request screen 740, the dental recommendation app 70 displays an X-ray upload screen 750, as illustrated in FIG. 7F where the user can upload his/her dental images (e.g., by selecting a local storage location of the dental images on his/her device or in a storage location in network communication therewith, such as cloud storage). After the dental image(s) are uploaded, the dental recommendation app 70 displays a dental image preview screen 760, as illustrated in FIG. 7G, for the user to confirm that the correct dental image(s) have been uploaded. If so, the user can press the analyze button 762 which causes the dental recommendation app 70 to analyze the uploaded dental image(s) according to the information provided through the X-ray analysis request screen 740.

FIG. 7H illustrates an X-ray analysis results screen 770. The X-ray analysis results screen 770 includes an annotated dental image 772, one or more apparent dental conditions 774, and a confidence score 776 of each apparent dental condition 774. Each apparent dental condition 774 also includes an information link 778 where the user can learn more information about the respective apparent dental condition 774.

Figure 7I:
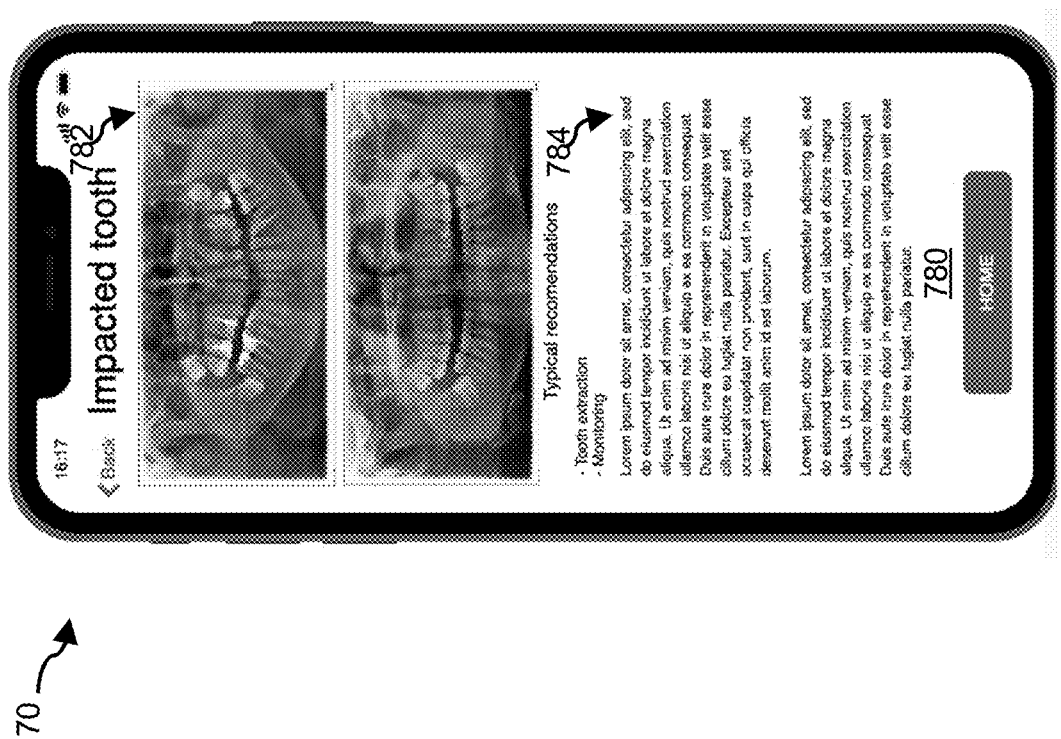

FIG. 7I illustrates an example impacted tooth information screen 780 that appears when the user activates the information link 778 of one of the apparent dental conditions 774 (e.g., the apparent dental condition 774 at the top of the list on screen 770). The impacted tooth information screen 780 includes annotated dental images 782 relating to the selected apparent dental condition 774 and a narrative 784 that describes the selected apparent dental condition 774. The narrative 784 can include common causes of the selected apparent dental condition 774, recommendations for improved dental hygiene, estimated costs to treat the selected apparent dental condition 774, and/or other information.

Aspects of the invention can offer among several advantages the ability to apply a non-biased and uniform common pathology. Common (e.g., panoramic) X-ray images can be used as the primary patient data to which the system and method are applied. A useful treatment plan can be determined and recommended to a patient, dental professional, or other user. Aspects of the invention can be employed by patients or practitioners as a virtual "second opinion" in the matter of deciding on dental procedures for a given patient.

Other optional features hereof include integration of genetic test analysis based on a patient's DNA tests. The artificial intelligence engine can also be programmed and configured to combine somatic pathology results, medical ultrasound data for a patient, histology data, biopsy data, cytology data, and/or other data when making analyses and recommendations.

A blockchain database and information management technique may further be optionally employed to securely and efficiently manage the personal and other information relating to a patient. These methods may be used for security or for improved efficiency of management of the dental information and dental images.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will appreciate the many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory, one or more floppy discs, compact discs, optical discs, magnetic tapes, flash memories, circuit configurations in field programmable gate arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various one or more of the aspects described above. In some embodiments, computer readable media may be non-transitory media.

The terms "program," "software," "app," and "application" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A non-transitory computer-readable medium storing instructions that, when executed by a computer having a hardware-based processor, cause the computer to:
   store a subject's dental images in a memory of the computer;
   automatically determine an apparent dental condition in the subject by analyzing the subject's dental images with an artificial neural network stored in the memory, the artificial neural network trained using manually-diagnosed dental images from other subjects;
   generate at least one output signal that represents the apparent dental condition; and
   generate a graphical output a representation of the apparent dental condition with respect to one of said dental images;
   wherein the instructions further cause the computer to store dental survey responses of the subject in the memory of the computer; and
   automatically determine the apparent dental condition in the subject by analyzing the dental images and the dental survey responses with the artificial neural network, the artificial neural network trained using the manually-diagnosed dental images from other subjects and a plurality of model dental survey response sets.

2. The non-transitory computer-readable medium of claim 1, wherein the instructions further cause the computer to determine a likelihood that the subject has the apparent dental condition, wherein the at least one output signal includes the likelihood.

3. The non-transitory computer-readable medium of claim 2, wherein the likelihood is quantitative.

4. The non-transitory computer-readable medium of claim 2, wherein the instructions further cause the computer to determine the likelihood based on a fit of the subject's dental images to the manually-diagnosed dental images used to train the artificial neural network.

5. The non-transitory computer-readable medium of claim 1, wherein the instructions further cause the computer to graphically annotate on the graphical output depicting said one of the subject's dental images to indicate which of the subject's teeth has the dental condition.

6. The non-transitory computer-readable medium of claim 5, wherein the instructions further cause the computer to graphically annotate the at least one of the subject's dental images to indicate a landmark structure in the subject's mouth.

7. The non-transitory computer-readable medium of claim 1, wherein the model dental survey response sets include hypothetical dental survey response sets from hypothetical patients.

8. The non-transitory computer-readable medium of claim 1, wherein the instructions further cause the computer to generate a dental information output signal that corresponds to dental information regarding the apparent dental condition.

9. The non-transitory computer-readable medium of claim 1, wherein the instructions further cause the computer to generate a dental cost estimate output signal that corresponds to a cost estimate for treating the apparent dental condition.

* * * * *